United States Patent

Wirth et al.

Patent Number: 5,380,344
Date of Patent: Jan. 10, 1995

[54] COMPOSITIONS COMPRISING 2,2',2''-NITRILOTRIETHANOL CYCLOMETALATES

[75] Inventors: Hermann O. Wirth, Bensheim; Hans-Helmut Friedrich, Lautertal, both of Germany

[73] Assignee: Ciba-Geigy Corporation, Ardsley, N.Y.

[21] Appl. No.: 99,874

[22] Filed: Jul. 30, 1993

Related U.S. Application Data

[62] Division of Ser. No. 638,601, Jan. 7, 1991, Pat. No. 5,256,323.

[30] Foreign Application Priority Data

Jan. 11, 1990 [CH] Switzerland ............. 85/90-8

[51] Int. Cl.$^6$ ................................ C10L 1/30
[52] U.S. Cl. ........................... 44/367; 44/317
[58] Field of Search ................... 44/367, 317

[56] References Cited

U.S. PATENT DOCUMENTS

| | | | |
|---|---|---|---|
| 2,312,208 | 2/1943 | Clayton et al. | 252/46.3 |
| 2,935,522 | 5/1960 | Samour | 260/429.5 |
| 2,957,840 | 10/1960 | Groszos et al. | 44/317 |
| 2,985,685 | 5/1961 | Thomas | 260/485 |
| 2,999,064 | 9/1961 | Sluhan | 252/49.6 |
| 3,009,791 | 11/1961 | Emrick | 44/317 |
| 3,118,921 | 1/1964 | Samonr | 252/49.6 |
| 3,118,955 | 1/1964 | Young | 260/652.5 |
| 3,125,525 | 3/1964 | Siegart et al. | 252/46.3 |
| 3,186,946 | 6/1965 | Sluhan | 252/49.6 |
| 3,224,971 | 12/1965 | Knowles et al. | 252/49.6 |
| 3,227,739 | 1/1966 | Versteeg | 260/462 |
| 3,483,271 | 12/1969 | Holoch et al. | 260/874 |
| 3,562,207 | 2/1971 | Ludwig | 260/45.8 |
| 3,598,757 | 8/1971 | Cyb | 252/400 |
| 3,645,901 | 2/1972 | Matson | 252/75 |
| 3,755,388 | 8/1973 | Ludwig | 260/404 |
| 3,804,875 | 8/1974 | Ludwig | 26/462 |
| 4,511,516 | 4/1985 | Holstedt et al. | 252/49.6 |
| 4,578,488 | 3/1986 | Rummo et al. | 556/56 |
| 4,762,628 | 8/1988 | Phillips et al. | 252/51.5 |
| 4,778,612 | 10/1988 | Wirth et al. | 252/42.7 |
| 4,859,354 | 8/1989 | Phillips et al. | 252/47.5 |
| 4,863,621 | 9/1989 | Wirth et al. | 252/47.5 |
| 4,886,610 | 12/1989 | Wirth et al. | 252/49.6 |
| 4,892,670 | 1/1990 | Mendelsan | 252/37 |
| 4,943,381 | 7/1990 | Phillips et al. | 252/51.5 |

FOREIGN PATENT DOCUMENTS

| | | |
|---|---|---|
| 0092755 | 11/1983 | European Pat. Off. . |
| 239536 | 9/1987 | European Pat. Off. . |
| 8602114 | 4/1986 | WIPO . |

OTHER PUBLICATIONS

Chem. Abstr. 92:120944q (1980) (month unknown).
Chem. Abstr. 78:11005s (1973) (month unknown).
Chem. Abstr. 91:192800j (1979) (month unknown).
Chem. Abstr. 102:62368; (1985) (month unknown).
Chem. Abstr. 112:217097c (1990) (month unknown).

*Primary Examiner*—Jerry D. Johnson
*Attorney, Agent, or Firm*—William A. Teoli, Jr.

[57] ABSTRACT

Compositions comprising
a) a functional liquid or an internal combustion engine fuel and
b) at least one compound of the general formula I

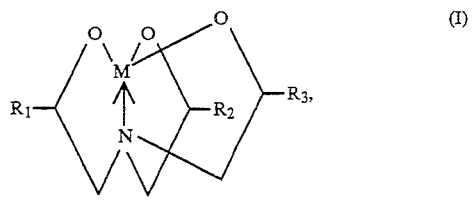

wherein $R_1$ is —$(CH_2—X)_n$—R, where X=—S— or —O—, n=0 or 1 and R is an alkyl group of 1 to 18 carbon atoms, a phenyl group, a phenyl group which is substituted by at least one $C_1$-$C_{18}$alkyl group, a phenyl-$C_1$-$C_4$alkyl group or a phenyl-$C_1$-$C_4$alkyl group which is substituted by at least one $C_1$-$C_4$alkyl group, or $R_1$ is an alkyl group of 1 to 18 carbon atoms which is substituted by at least one OH group, or $R_1$ is a (Abstract continued on next page.)

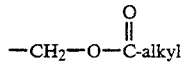

group in which the alkyl moiety contains 1 to 18 carbon atoms, and $R_2$ and $R_3$ are the same or different and are —H or, independently of $R_1$, have the same meanings as $R_1$, and M is B, Al, Fe, Cr, Sb or Bi, or M is a group M'—R' or a group M'—OR'', where M' is Ti, Zr or Sn, and R' and R'' is $C_1$-$C_{18}$alkyl or R' is

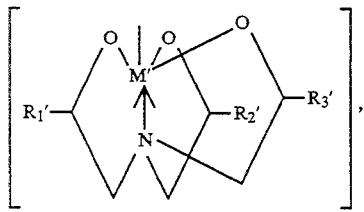

wherein M' is as defined above, and $R_1'$, $R_2'$ and $R_3'$ have the meanings of $R_1$, $R_2$ and $R_3$, or R'' is Li, Na or K or is

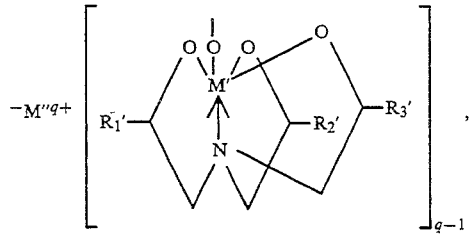

wherein M' is as defined above and M'' is Mg, Ca, B, Al, Fe, Cr, Sb, Bi, Zn, Ti, Ni or Cu, q has the valence of M'', and $R_1'$, $R_2'$ and $R_3'$ have the respective meanings of $R_1$, $R_2$ and R, or M is —VO.

The compounds of formula act, for example, in lubricants as antiwear additives and extreme pressure additives, and also as stabilisers for natural or regenerated polymers.

8 Claims, No Drawings

COMPOSITIONS COMPRISING 2,2',2''-NITRILOTRIETHANOL CYCLOMETALATES

This is a divisional of Ser. No. 07/638,601, filed Jan. 7, 1991 now U.S. Pat. No. 5,256,323.

The present invention relates to novel compositions comprising 2,2',2''-nitrilotriethanol cyclometalates (triethanolamine cyclometalates), to compounds of the series of the 2,2',2''-nitrilotriethanol cyclometalates, to a novel process for the preparation of said compounds, and to the use thereof.

Compounds of formula

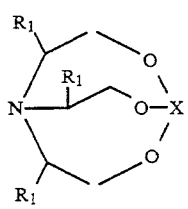

wherein X=Al, B or SiMe and $R_1$=Me or cyclohexyl, have been disclosed in Chemical Abstracts 91, 1979, 192 800j, for purifying $C_4$ hydrocarbon fractions from the pyrolysis of petroleum.

Cyclic borates as pan of an antioxidant mixture for stabilising synthetic resins are known from U.S. Pat. No. 3,598,757. Such borates may have the formula

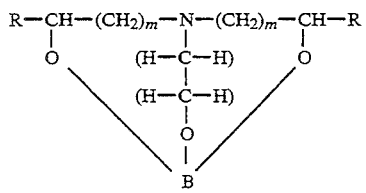

wherein R is —H, alkyl, alkylene, aminoalkyl, dialkylaminoalkyl, cycloalkylaminoalkyl, alkoxyalkyl, hydroxyalkyl, alkylenoxyalkyl, aryl or aryloxyalkyl, where alkyl or alkylene may each contain one to four carbon atoms, and m=1 or 2.

Compounds of the general formula

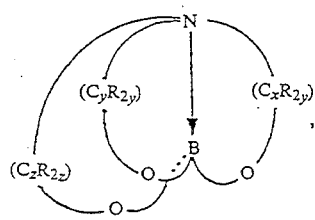

wherein x, y and z are integers from 2 to 4 and R may be —H, alkyl, cycloalkyl, alkenyl and cycloalkenyl, aryl, hydroxyl-substituted lower alkyl or radicals of formulae $R_nOC$—$R_m$ or

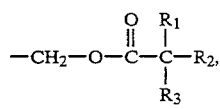

are disclosed in U.S. Pat. Nos. 3,755,388 and 3,804,875 and in DE-OS 19 08 844. Such compounds are antistatic agents in polymeric fibres and films and are useful as colour improvers for fatty acid distillations.

Salts having anions of the type

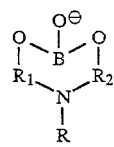

wherein R is an inorganic or organic radical and $R_1$ and $R_2$ are organic radicals, and the cation may be of organic or inorganic nature or hydrogen, have been proposed as extreme pressure additives for lubricants in U.S. Pat. No. 4,892,670.

Novel compositions have now been found which contain 2,2',2''-nitriloethanol cyclometalates as well as novel utilities for 2,2',2''-nitriloethanol cyclometalates.

The novel compositions of this invention comprise
a) a functional fluid or an internal combustion engine fuel, and
b) at least one compound of the general formula I

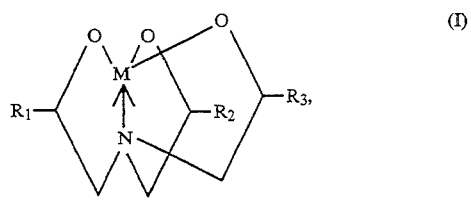

wherein $R_1$ is —$(CH_2—X)_n$—R, where X=—S— or —O—, n=0 or 1 and R is an alkyl group of 1 to 18 carbon atoms, a phenyl group, a phenyl group which is substituted by at least one $C_1$-$C_{18}$alkyl group, a phenyl-$C_1$-$C_4$alkyl group or a phenyl-$C_1$-$C_4$alkyl group which is substituted by at least one $C_1$-$C_4$alkyl group, or $R_1$ is an alkyl group of 1 to 18 carbon atoms which is substituted by at least one OH group, or $R_1$ is a

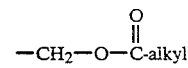

group in which the alkyl moiety contains 1 to 18 carbon atoms, and $R_2$ and $R_3$ are the same or different and are —H or, independently of $R_1$, have the same meanings as $R_1$, and M is B, Al, Fe, Cr, Sb or Bi, or M is a group M'—R' or a group M'—OR'', where M' is Ti, Zr or Sn, and R' and R'' are $C_1$-$C_{18}$alkyl or R' is

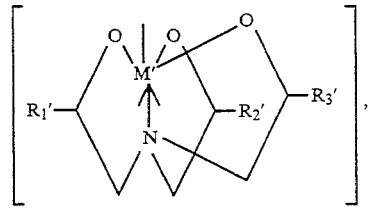

wherein M' is as defined above, and $R_1'$, $R_2'$ and $R_3'$ have the meanings of $R_1$, $R_2$ and $R_3$, or R'' is Li, Na or K or is

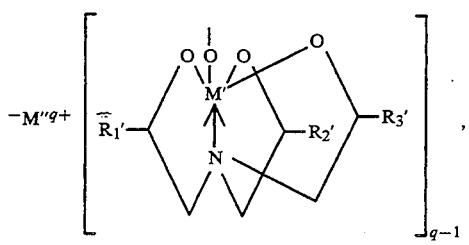

wherein M' is as defined above and M" is Mg, Ca, B, Al, Fe, Cr, Sb, Bi, Zn, Ti, Ni or Cu, q has the valency of M", and $R_1'$, $R_2'$ and $R_3'$ have the respective meanings of $R_1$, $R_2$ and R, or M is —VO.

Useful compositions are those comprising compounds of formula I above, wherein M is

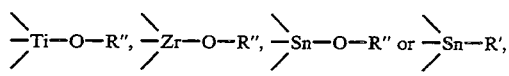

wherein R' and R" are alkyl of 1 to 18 carbon atoms.

Further useful compositions are those comprising compounds of formula I above, wherein M is B, Al, Fe, VO or Ti—O—$C_4$-$C_8$alkyl. Other useful compositions are those comprising compounds of formula I, wherein $R_1$ is —$CH_2$—S—$C_4$-$C_{12}$alkyl, —$CH_2$—O—$C_4$-$C_{12}$alkyl, —$CH_2$—O—CO—$C_4$-$C_{12}$alkyl,

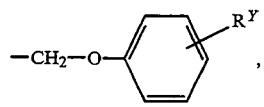

wherein $R^Y$=alkyl of 4 to 18 carbon atoms, or is

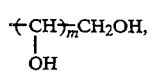

wherein m=1, 2 or 3, and $R_2$ and $R_3$ are each independently of the other H or $R_1$.

Preferred compositions comprise compounds of formula I above, wherein $R_1$ is as defined above and $R_2$ and $R_3$ are hydrogen, or wherein $R_1$ and $R_2$ have the above meanings, with the exception of hydrogen, and $R_3$ is hydrogen.

Particularly preferred compositions are those comprising compounds of formula I above, wherein $R_1$ is —$CH_2$—S—$C_4$-$C_{12}$alkyl, —$CH_2$—O—CO—$C_8$-$C_{12}$alkyl, and $R^2$ and $R^3$ are —H.

Further particularly preferred compositions are those comprising compounds of formula I above, wherein $R_1$ and $R_2$ are —$CH_2$—S—$C_4$-$C_{12}$alkyl and $R_3$ is —H.

Preferred compositions also comprise those which contain compounds of formula I, wherein $R_1$ is an alkyl group of 1 to 18 carbon atoms which is substituted by at least one OH group, and $R_2$ and $R_3$ are —($CH_2$—X)$_n$—R, in which the particularly preferred meaning of X is again —S—.

R, R' or R" as an alkyl group of 1 to 18 carbon atoms is typically methyl, ethyl, propyl, isopropyl, n-butyl, isobutyl, tert-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl, 1,1,3,3-tetramethylhexyl or 1-methylundecyl.

R, R' and R" are preferably $C_4$-$C_{12}$alkyl, and are most preferably $C_4$-$C_9$alkyl.

R, R' and R" may be tert-butyl, 2-ethylhexyl, tert-nonyl, n-decyl and tert-dodecyl.

Tert-nonyl and tert-dodecyl will be understood as meaning, respectively, 1,1,3,3-tetramethylpentyl 1,1,3,3-tetramethyloctyl.

R' and R" are most preferably n-butyl.

R as a phenyl-$C_1$-$C_4$alkylgruppe may be benzyl or phenethyl. The phenyl moiety may be substituted by at least one $C_1$-$C_4$alkyl group, one or two $C_1$-$C_4$alkyl groups being suitable and one $C_1$-$C_2$alkyl group being preferred.

$R_1$, $R_2$ or $R_3$ as an alkyl group of 1 to 18 carbon atoms which is substituted by at least one OH group may be a group of formula

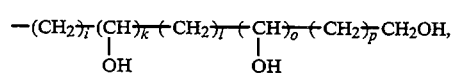

wherein i, k, l, o und p are each an integer from 0 to 17 and the sum of i+k+l+o+p together is not more than 17. By analogy, branched carbon chains are also comprised.

A group of formula

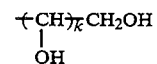

is preferred, wherein k is 1, 2 or 3. The preferred value of k is 3.

Preferred groups are accordingly:

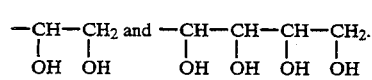

Where $R_1$, $R_2$ or $R_3$ is

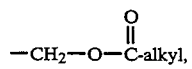

the alkyl moiety contains 1 to 18 carbon atoms, conveniently 4–12 carbon atoms and, preferably, 4–9 carbon atoms. Representative examples of alkyl groups are those cited above.

Particularly preferred groups for $R_1$ as

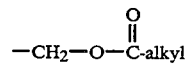

are typically

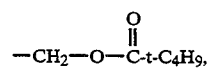

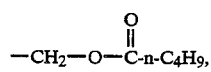

-continued

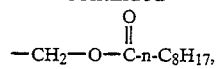

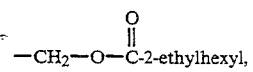

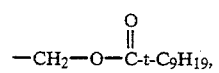

and

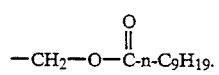

Where R is a phenyl group which is substituted by an alkyl group of 1 to 18 carbon atoms, said alkyl group is selected from those previously cited above.

R is preferably a phenyl group which is substituted by 1, 2 or 3 alkyl groups of 1 to 12 carbon atoms. Most preferably R is a phenyl group which is substituted by a $C_1$–$C_{12}$ alkyl group.

Preferred are groups such as

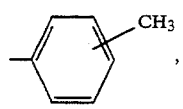

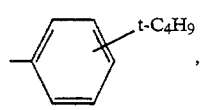

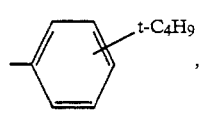

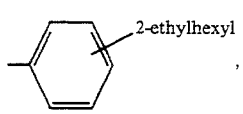

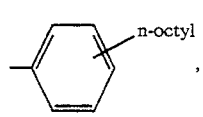

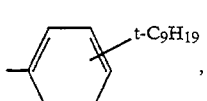

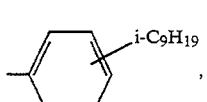

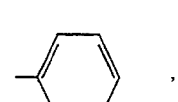

Exemplary of preferred compositions are those which contain the following compounds:

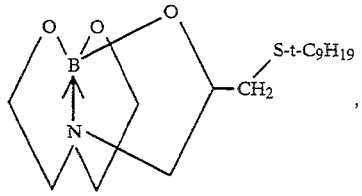

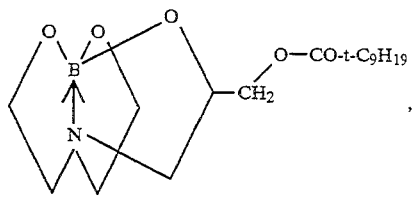

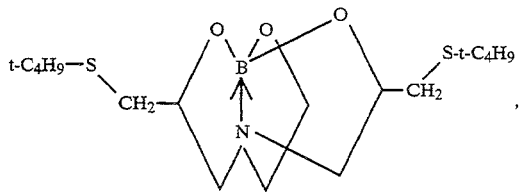

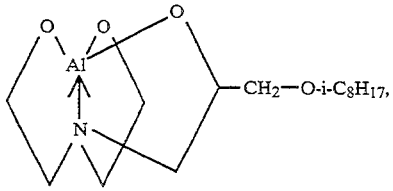

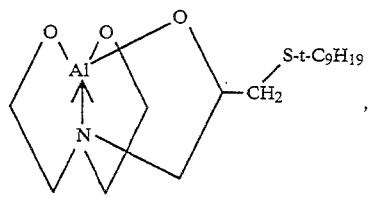

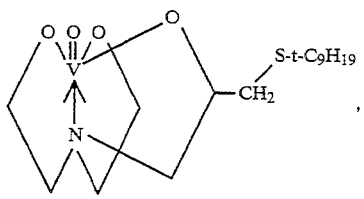

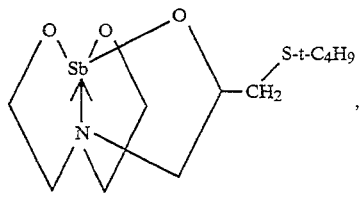

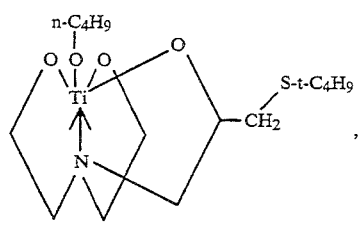

-continued

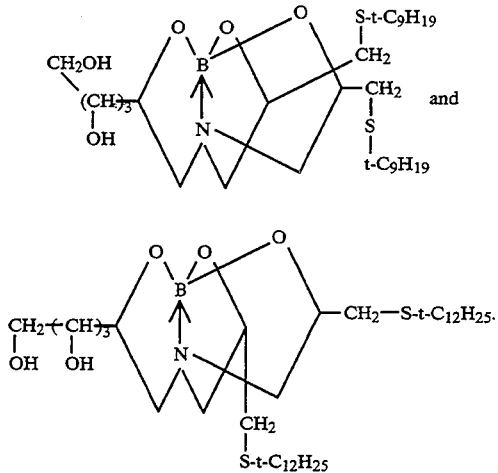

Exemplary of particularly preferred compounds are:

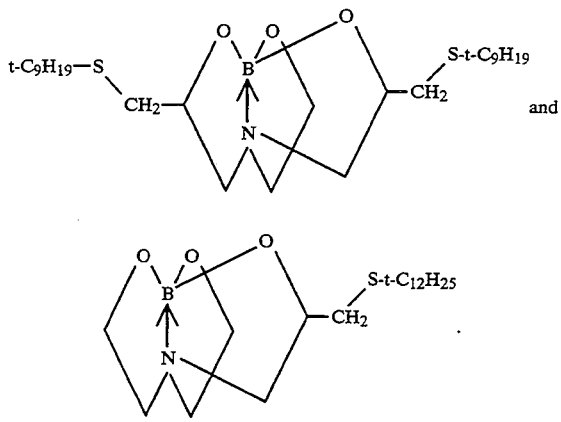

A further group of compounds of formula I which are of particular importance in compositions of this invention comprises those of the general formula I in which M=M'—OR", where R"=M"

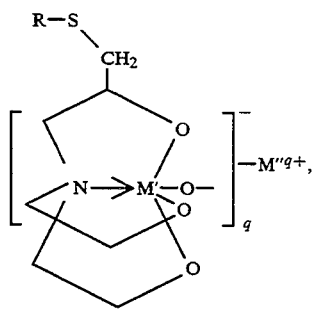

wherein q, R and M' are as defined above and M" is preferably B, Al, Fe, Cr, Sb, Bi, Zn, Ti or Cu and, most preferably, Ti, B, Al, Fe or Zn, and q has the valency of M".

Illustrative of a compound of the last mentioned kind is

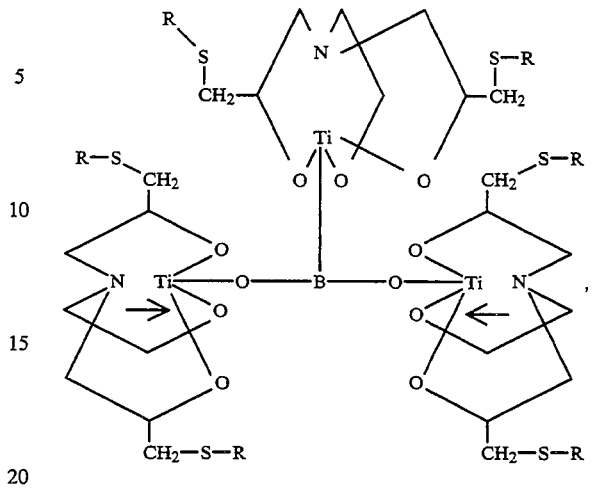

wherein R may have one of the aforementioned meanings.

The compounds of formula I are especially suitable for imparting improved performance properties to functional fluids. It is taught, for example, in U.S. Pat. No. 4,557,843 that boron-containing heterocyclic compounds bring about an enhancement of the extreme pressure and wear properties in lubricants. It has now been found that the aforementioned compounds of formula I surprisingly impart improved properties to functional fluids. Hence the invention also encompasses compositions comprising a functional fluid and at least one compound of the general formula I as indicated above.

Illustrative examples of functional fluids are lubricants, hydraulic fluids and metal processing fluids.

Suitable lubricants may be those based on mineral or synthetic oils or mixtures thereof, or on vegetable and animal oils, fats and waxes. The lubricants are known to the skilled person and described in the relevant literature, for example in Dieter Klamann, "Lubricants and Related Products" (Verlag Chemie, Weinheim/Deerfield Beach/Basel, 1984), in Schewe-Kobek, "Das Schmiermittel-Taschenbuch" (Dr. Alfred Hüthig-Verlag, Heidelberg, 1974) and in "Ullmanns Enzyklopädie der technischen Chemie", Vol. 13, pages 85-94 (Verlag Chemie, Weinheim, 1977).

The lubricants are preferably oils, but also comprise fats based on a mineral oil.

The mineral oils are based preferably on hydrocarbon compounds.

Synthetic lubricants typically comprise lubricants based on aliphatic or aromatic carboxylates, polymeric esters, polyalkylene oxides, phosphates, poly-α-olefins or silicones, on a diester of a divalent acid with a monohydric alcohol, for example dioctyl sebacate or dinonyl adipate, on a triester of trimethylolpropane with a monovalent acid or with a mixture of such acids, for example trimethylolpropane tripelargonate, trimethylolpropane tricaprylate or mixtures thereof, on a tetraester of pentaerythritol with a divalent acid or with a mixture of such acids, for example pentaerythritol tetracaprylate, or on a complex ester of monovalent and divalent acids with polyhydric alcohols, for example a complex ester of trimethylolpropane with caprylic and sebacic acid or of a mixture thereof. Especially suitable are, in addition to mineral oils, for example poly-α-olefins, ester-based lubricants, phosphates, glycols, polyglycols and polyalkylene glycols, and mixtures thereof with water.

Suitable vegetable oils are the oils, fats and waxes which may be obtained from olives, palms, palm nuts, beet, rape, linseeds, ground nuts, soybeans, cotton seeds, castor oil plants, sunflower seeds, pumpkin seeds, coconuts, maize or their modified forms such as sulfated or epoxidised oils, for, example epoxidised soybean oil, as well as mixtures of these substances. Illustrative examples of animal oils, fats and waxes which may be used as lubricants are tallows, fish oils, sperm oils, neat's foot oil, lard oils and the modified forms and mixtures thereof.

The compositions may contain the compounds of formula I described above in amounts of 0.01 to 10% by weight, conveniently 0.03 to 5% by weight, preferably 0.05 to 3% by weight and, most preferably, 0.5 to 1.5% by weight, based on said composition.

The compounds of formula I may be mixed with the functional fluid in a manner known per se. The compounds are readily soluble in oils. It is also possible to prepare a masterbatch, which can be diluted in accordance with the consumption to suitable concentrations with the appropriate functional fluid.

The functional fluids, and especially the lubricants, may also contain other additives which are added for further enhancement of the basic properties of said fluids. Such additional additives comprise antioxidants, metal deactivators, rust inhibitors, viscosity index improvers, pour-point depressants, dispersants, detergents and other antiwear additives. Illustrative examples of these additives are:

1. Alkylated monophenols 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, o-tert-butylphenol.

2. Alkylated hydroquinones 2,6-di-tert-butyl-4-methoxyphenol, 2,5-di-tert-butylhydroquinone, 2,5-di-tert-amylhydroquinone, 2,6-diphenyl-4-octadecyloxyphenol.

3. Hyroxylated thiodiphenyl ethers 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

4. Alkylidenebisphenols 2,2'-methylenebis(6-tert-butyl-4-methylphenol), 2,2'-methylenebis( 6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methyl-benzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methyl-phenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4methylphenyl]terephthalate.

5. Benzyl compounds 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithiolterephthalate, 1,3,5-tris(3,5-di-tert-butyl-4-hydroxybenzyl) isocyanurate, 1,3,5-tris(4-tert-butyl3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl)isocyanurate.

6. Acylaminophenols 4-hydroxylauranilide, 4-hydroxystearanilide, 2,4-bis-(octylmercapto)-6-(3,5-di-tert-butyl-4-hydroxyanilino)-s-triazine, octyl N-(3,5-di-tert-butyl-4-hydroxyphenyl)-carbamate.

7. Esters of $\beta$-(3,5-di-tert-butyl-4-hydroxyphenyl)propionic acid with mono- or polyhydric alcohols, e.g. with methanol, diethylene glycol, octadecanol, 1,6-hexanediol, neopentyl glycol, triethylene glycol, pentaerythritol, tris(hydroxyethyl) isocyanurate, thiodiethylene glycol, bis(hydroxyethyl)oxalodiamide.

8. Esters of $\beta$-(5-tert-butyl-4-hydroxy-3-methylphenyl)propionic acid with mono- or polyhydric alcohols, e.g. with methanol, diethylene glycol, octadecanol, triethylene glycol, 1,6-hexanediol, pentaerythritol, neopentyl glycol, tris(hydroxyethyl) isocyanurate, thiodiethylene glycol, N,N'-bis(hydroxyethyl)oxalodiamide.

9. Amides of $\beta$-(3,5-di-tert-butyl-4-hydroxyphenyl)propionic acid e.g. N,N'-bis( 3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)-hydrazine.

Examples of amine antioxidants

N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(naphthyl-2)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfonamido)-diphenylamine, N,N'-dimethyl-N,N'-di-sec-butyl-p-phenylenediamine, diphenylamine, N-allyldiphenylamine, 4-iso-propoxydiphenylamine, N-phenyl-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, mixture of mono- and dialkylated tert-butyl/tert-octyldiphenylamines, 2,3-dihydro-3,3-dimethyl-4H-1,4-benzothiazine, phenothiazine, N-allylphenothiazine.

Examples of further antioxidants

Aliphatic or aromatic phosphites, esters of thiodipropionic acid or of thiodiacetic acid, or salts of dithiocarbamic or dithiophosphoric acid.

Examples of metal deactivators, for example for copper, are triazoles, benzotriazoles and derivatives thereof, tolutriazoles and derivatives thereof, 2-mercaptobenzothiazole, 2-mercaptobenzotriazole, 2,5-dimercaptobenzotriazole, 2,5-dimercaptobenzothiadiazole, 5,5'-methylenebisbenzotriazole, 4,5,6,7-tetrahydrobenzotriazole, salicylidene propylenediamine, salicylaminoguanidine and the salts thereof.

Examples of rust inhibitors are a) organic acids and the esters, metal salts and anhydrides thereof, for example:
   N-oleoyl sarcosine, sorbitan monooleate, lead naphthenate, alkenylsuccinic anhydride, for example dodecenylsuccinic anhydride, alkenylsuccinic partial esters and partial amides, 4-nonylphenoxyacetic acid.
b) Nitrogen-containing compounds, for example:
   I. Primary, secondary or tertiary aliphatic or cycloaliphatic amines and amine salts of organic and inorganic acids, for example oil-soluble alkylammonium carboxylates.
   II. Heterocyclic compounds, for example: substituted imidazolines and oxazolines.
c) Phosphorus-containing compounds, for example:
   amine salts of phosphoric acid partial esters or phosphonic acid partial esters, zinc dialkyldithiophosphates.
d) Sulfur-containing compounds, for example:
   barium dinonylnaphthalene sulfonates, calcium petroleum sulfonates.

Examples of viscosity index improvers are polyacrylates, polymethacrylates, vinyl pyrrolidone/methacrylate copolymers, polyvinylpyrrolidones, polybutenes, olefin copolymers, styrene/acrylate copolymers, polyethers.

Examples of pour-point depressants are polymethacrylates, alkylated naphthalene derivatives.

Examples of dispersants/surfactants are polybutenylsuccinamides or-imides, polybutenylphosphonic acid derivatives, basic magnesium, calcium, and barium sulfonates and phenolates.

Examples of antiwear additives are sulfur and/or phosphorus and/or halogen-containing compounds such as sulfonated vegetable oils, zinc dialkyl dithiophosphates, tritolylphosphate, chlorinated paraffins, alkyl and aryldi- and trisulfides, triphenylphosphorothionates, diethanolaminomethyltolyltriazole, bis(2-ethylhexyl)aminomethyltolyltriazole.

The present invention also relates to the use of compounds of the general formula I as indicated above as antiwear and extreme pressure additives for functional fluids.

The invention further relates to compositions comprising an internal combustion engine fuel and at least one compound of formula I as indicated above.

The internal combustion engine fuels are typically the fuels for gas turbines and for lifting piston and rotary piston engines with self-ignition or spark-ignition (diesel or Otto principle). The fuels are accordingly gaseous or, in particular, liquid hydrocarbonaceous compounds and mixtures thereof, for example of the series of methane, ethane, propane, butane and, preferably, the higher hydrocarbon compounds such as those of the octane series, kerosene and the like, and mixtures thereof, known as motor fuels and diesel oils (diesel fuels), and also alcohols such as methanol and ethanol or, for example, vegetable oils such as sunflower oil or rape oil. Diesel fuel is preferred.

Suitable and preferred compounds of formula I as indicated above result in suitable and preferred compositions.

The compounds of formula I are added to the compositions containing the internal combustion engine fuel typically in amounts of 0.00001 to 1% by weight, conveniently 0.0001 to 0.1% by weight, preferably 0.0001 to 0.1% by weight and, most preferably, 0.001 to 0.1% by weight, based on the composition.

It is, for example, possible to prepare a 1 to 50% by weight solution of the compound of formula I with a solvent, for example a higher hydrocarbon fraction such as petroleum, or from the combustion engine fuel, preferably the diesel fuel, and to effect metered addition of this concentrated solution, while the engine is running, to a main flow of the fuel fed to the engine such that compositions of the combustion engine fuel and compounds of formula I are formed in concentrations as described above. These compositions then constitute the fuel to be burned in the engine. This concentrated solution can, however, also be added direct to the fuel in order thereby to simplify addition.

Such fuel compositions result in improved combustion and in exhaust fumes which contain fewer contaminants. For example, the emission of soot and nitrogen oxides in the exhaust fumes of engines which operate according to the diesel principle can be reduced.

The invention also relates to the use of the compounds of formula I as claimed in claim 1 as additives for internal combustion engine fuels.

The compounds of formula I can also be used as stabilisers, for example processing stabilisers, in natural, regenerated or man-made organic materials, especially in thermoplastics. Illustrative examples of such plastics materials are:

1. Polymers of monoolefins and diolefins, for example polypropylene, polyisobutylene, polybut-1-ene, polymethylpent-1-ene, polyisoprene or polybutadiene, as well as polymers of cycloolefins, for example of cyclopentene or norbornene, polyethylene (which can be uncrosslinked or crosslinked), for example high density polyethylene (HDPE), low density polyethylene (LDPE and linear low density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers linear low density polyethylene (LLDPE) and mixtures thereof with low density polyethylene (LDPE), propylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate or ethylene/acrylic acid copolymers and their salts (ionomers), as well as terpolymers of ethylene with propylene and a diene such as hexadiene, dicyclopentadiene or ethylidenenorbornene; and also mixtures of such copolymers with each other and with polymers mentioned in 1 ) above, for example polypropylene/ethylene propylene copolymers, LDPE/EVA, LDPE/EAA, LLDPE/EVA and LLDPE/EAA.

3a. Hydrocarbon resins (for example $C_5$–$C_9$), including hydrogenated modifications thereof (for example tackifiers).

4. Polystyrene, poly-(p-methylstyrene), poly-(α-methylstyrene).

5. Copolymers of styrene or α-methylstyrene with dienes or acrylic derivatives, for example styrene|[ch]butadiene, styrene/acrylonitrile, styrene/alkylmethacrylate, styrene/butadiene/alkylacrylate, styrene/maleic anhydride, styrene/acrylonitrile/methyl acrylate; mixtures of high impact strength from styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or α-methylstyrene, for example styrene on polybutadiene, styrene on polybutadiene/styrene or polybutadiene/acrylonitrile; styrene and acrylonitrile (or methacrylonitrile) on polybutadiene; styrene and maleic anhydride or maleimide on polybutadiene; styrene, acrylonitrile and maleic anhydride or maleimide on polybutadiene; styrene, acrylonitrile and methyl methacrylate on polybutadiene, styrene and alkyl acrylates or methacrylates on polybutadiene, styrene and acrylonitrile on ethylene/propylene/diene terpolymers, styrene and acrylonitrile on polyalkylacrylates or polyalkylmethacrylates, styrene and acrylonitrile on acrylate/butadiene copolymers, as well as mixtures thereof with the copolymers listed under 5), for example the copolymer mixtures known as ABS, MBS, ASA or AES polymers.

7. Halogenated polymers such as polychloroprene, chlorinated rubbers, chlorinated or sulfochlorinated polyethylene, copolymers of ethylene and chlorinated ethylene, epichlorohydrin homo- and copolymers, preferably polymers of halogenated vinyl compounds, for example poly- vinylchloride, polyvinylidene chloride, polyvinyl fluoride, polyvinylidene fluoride, as well as copolymers thereof, for example vinyl chloride/vinylidene chloride, vinyl chloride/vinyl acetate or vinylidene chloride/vinyl acetate copolymers.

8. Polymers derived from α,β-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkylacrylate copolymers, acrylonitrile/alkoxyalkylacrylate or acrylonitrile/vinyl halide copolymers or acrylonitrile/alkylmethacrylate/butadiene terpolymers.

10. Polymers derived from unsaturated alcohols and amines or the acyl derivatives or acetals thereof, such as polyvinyl alcohol, polyvinyl acetate, polyvinyl stearate, polyvinyl benzoate, polyvinyl maleate, polyvinylbutyrate, polyallyl phthalate or polyallylmelamine; as well as their copolymers with the olefins mentioned in 1) above.

11. Homopolymers and copolymers of cyclic ethers such as polyalkylene glycols, polyethylene oxide, polypropylene oxide or copolymers thereof with bisglycidyl ethers.

12. Polyacetals such as polyoxymethylene and those polyoxymethylenes which contain ethylene oxide as a comonomer, polyacetals modified with thermoplastic polyurethanes, acrylates or MBS.

13. Polyphenylene oxides and sulfides and mixtures thereof with polystyrene or polyamides.

14. Polyurethanes which are derived from polyethers, polyesters or polybutadienes carrying terminal hydroxyl groups on the one hand and aliphatic or aromatic polyisocyanates on the other, as well as precursors thereof.

15. Polyamides and copolyamides which are derived from diamines and dicarboxylic acids and|[ch]or from aminocarboxylic acids or the corre- sponding lactams, such as polyamide 4, polyamide 6, polyamide 6/6, 6/10, 6/9, 6/12 and 4/6, polyamide 11, polyamide 12, aromatic polyamides obtained by condensation of m-xylene, diamine and adipic acid; polyamides prepared from hexamethylenediamine and isophthalic and/or terephthalic acid, with or without an elastomer as modifier, for example poly-2,4,4,-trimethylhexamethylene terephthalamide or poly-m-phenylene isophthalamide; block copolymers of the aforementioned polyamides with polyolefins, olefin copolymers, ionomers or chemically bonded or grafted elastomers; or with polyethers, for example with polyethylene glycol, polypropylene glycol or polytetramethylene glycol; and also polyamides or copolyamides modified with EPDM or ABS, and polyamides condensed during processing (RIM polyamide systems).

16. Polyureas, polyimides and polyamide-imides and polybenzimidazoles.

17. Polyesters derived from dicarboxylic acids and diols and/or from hydroxycarboxylic acids or the corresponding lactones, such as poly-ethylene terephthalate, polybutylene terephthalate, poly-1,4-dimethylolcyclohexane terephthalate, polyhydroxybenzoates as well as block-copolyether esters derived from hydroxyl-terminated polyethers; and also polyesters modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins derived from substituted acrylic esters such as epoxy acrylates, urethane acrylates or polyester acrylates.

24. Alkyd resins, polyester resins or acrylate resins which are cross-linked with melamine resins, urea resins, polyisocyanates or epoxy resins.

25. Crosslinked epoxy resins which are derived from polyepoxides, for example from bisglycidyl ethers or from cycloaliphatic diepoxides.

26. Natural polymers such as cellulose, rubber, gelatine and chemically modified homologous derivatives thereof such as cellulose acetates, cellulose propionates and cellulose butyrates, or the cellulose ethers, such as methylcellulose; as well as rosins and their derivatives.

27. Mixtures (polyblends) of the aforementioned polymers, for example PP/EPDM, Polyamide 6/EPDM or ABS, PVC/EVA, PVS/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPE/HIPS, PPE/PA 6.6 and copolymers, PA/HDPE, PA/PP, PA/PPE.

28. Naturally occurring and synthetic organic materials which are pure monomeric compounds or mixtures of such compounds, for example mineral oils, animal and vegetable fasts, oil and waxes, or oils, fats and waxes based on synthetic esters (e.g. phthalates, adipates, phosphates or trimellitates) and also the mixtures of synthetic esters with mineral oils in any weight ratios which are used as spinning compositions, as well as aqueous emulsions of such materials.

29. Aqueous emulsions of natural or synthetic rubber, for example natural latex or latices of carboxylated styrene/butadiene copolymers.

The compounds of formula I are obtainable by a novel process, which comprises reacting a compound of formula II

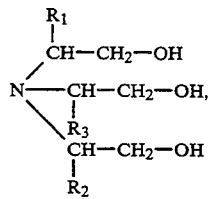
(II)

wherein $R_1$, $R_2$ and $R_3$ are as defined above, with a compound of formula III

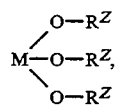
(III)

wherein $R^Z$ is —H or $C_1$-$C_8$alkyl, and M is as defined above.

$R^Z$ as $C_1$-$C_8$alkyl may typically be methyl, ethyl, n-propyl, isopropyl, n-butyl, tert-butyl, n-pentyl, n-hexyl or n-octyl. Preferably $R^Z$ is —H, methyl, ethyl or isopropyl.

All substituents $R^Z$ are preferably identical.

The compounds of formula II are disclosed, for example, in EP-A 0 233 140. The compounds of formula III are known, can be prepared by known processes, or are commercial products such as boric acid or triethyl borate.

The process can be carried out by using the compounds of formula II and III in equimolar ratio or in an excess of one or other component of up to 10% by weight. A solvent may be used. It is also possible to carry out the process without a solvent, for example if the reactants are soluble in each other or are dissolved in each other by melt fusion. Suitable solvents are all solvents which are inert to the reactants, for example cyclohexane, toluene, ethanol or mixtures thereof.

The reaction mixture is normally kept, with stirring, in the temperature range from room to reflux temperature. The reaction is conveniently carried out at reflux temperature. Reaction temperatures higher than 150° C. are normally not necessary, so that the process can also be carried out before reflux temperature is reached, especially if this latter should be higher than, for example, 120° C. and, in particular, 150° C.

The reaction time is not crucial and may be, for example, from 15 minutes to 2 hours.

The final product can be obtained in a manner known per se and, if desired or necessary, purified.

Some of the compounds of formula I are novel.

Accordingly, the invention further embraces compounds of the general formula I

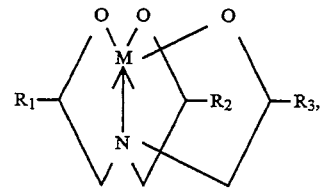

wherein M is B and $R_1$ is —$CH_2$—S—R, wherein R is an alkyl group of 1 to 18 carbon atoms, a phenyl group, a phenyl group which is substituted by at least one $C_1$-$C_{18}$ alkyl group, a phenyl-$C_1$-$C_4$alkyl group or a phenyl-$C_1$-$C_4$alkyl group which is substituted by at least one $C_1$-$C_4$alkyl group, and $R_2$ and $R_3$ are each independently of the other —H or, independently of $R_1$, have the same meanings as $R_1$, or compounds of formula I, wherein M is Al, Fe, Cr, Sb, Bi or VO and $R_1$ is —$(CH_2$—$X)_n$—R, wherein X=—S— or —O—, n=0 or 1 and R is an alkyl group of 1 to 18 carbon atoms, a phenyl group or a phenyl group which is substituted by at least one $C_1$-$C_{18}$alkyl group, a phenyl-$C_1$-$C_4$alkyl group or a phenyl-$C_1$-$C_4$alkyl group which is substituted by at least one $C_1$-$C_4$alkyl group, or $R_1$ is an alkyl group of 1 to 18 carbon atoms which is substituted by at least one OH group, or $R_1$ is a

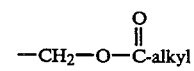

group, in which the alkyl moiety contains 1 to 18 carbon atoms, and $R_2$ and $R_3$ are the same or different and are —H or, independently of $R_1$, have the same meanings as $R_1$, or compounds of formula I, wherein M is a M'—R' group or a M'—OR" group, wherein M' is Ti, Zr or Sn, and R' and R" are $C_1$-$C_{18}$alkyl, or R' is

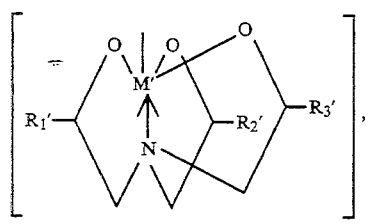

wherein M' is as defined above and $R_1'$, $R_2'$ and $R_3'$ have the meanings of $R_1$, $R_2$ and $R_3$, as indicated above, or R" is Li, Na or K or is

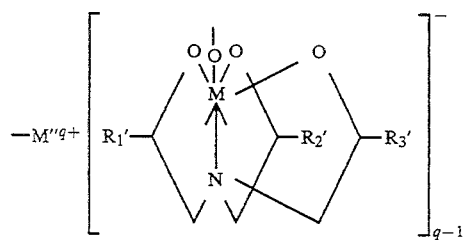

wherein M' is as defined above and M" is Mg, Ca, B, Al, Fe, Cr, Sb, Bi, Zn, Ti, Ni, Cu or Pb, q has the valency of M" and $R_1'$, $R_2'$ and $R_3'$ each have the respective meanings of $R_1$, $R_2$ and $R_3$.

Preferred compounds of formula I are those wherein $R_1$ is —$CH_2$—S—R, where R is an alkyl group of 1 to 18 carbon atoms, and $R_2$ and $R_3$ are each independently —H or $C_1$-$C_{12}$alkyl which is substituted by up to 6 hydroxyl groups, or, independently of $R_1$, have the same meanings as $R_1$.

The following Examples illustrate the invention in more detail. All parts and percentages are by weight, unless otherwise stated.

Example 1

32.1 g of the compound t—$C_9H_{19}$—S—$CH_2$—CH(OH)—$CH_2$—N(—$CH_2$—$CH_2$—OH)$_2$, 6.2 g of boric acid and 150 ml of cyclohexane are charged to a 0.5 litre 3-necked flask fitted with water separator, reflux condenser, KPG stirrer and thermometer. With stirring, the mixture is heated to reflux and the water of reaction is removed (4,5 ml; cal. 5.4 ml). After cooling to 20° C., the precipitated crystals are filtered with suction, washed with cyclohexane and dried, giving the compound of formula

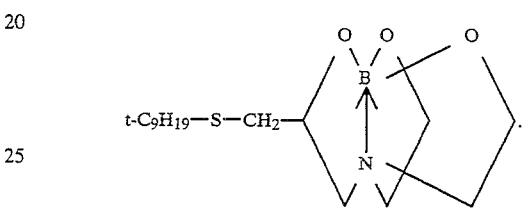

Yield: 22.4 g (=68% of theory) of white crystals which melt at 93° C.

Further compounds which are listed in Table I are prepared in accordance with the process described in this Example.

TABLE I

| Example | Formula | Analyt. data | Comments |
|---|---|---|---|
| 2 | | m.p. 83° C. | recrystallised. from $Et_2O$ |
| 3 | | | wax-like substance |
| 4 | | m.p. 180° C. | |
| 5 | | $n_D^{40}$: 1.4985 | |

TABLE I-continued

| Example | Formula | Analyt. data | Comments |
|---|---|---|---|
| 6 | 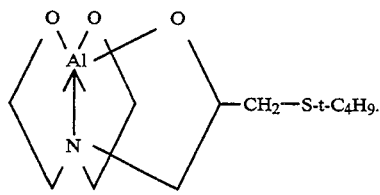 | | resin |

Example 7

32.1 g of the compound t—$C_9H_{19}$—S—$CH_2$—CH(OH)—$CH_2$—N(—$CH_2$—$CH_2$—OH)$_2$ and 20.4 g of aluminium triisopropylate are heated to 150° C. under nitrogen in a 100 ml 2-necked flask fitted with magnetic stirrer, distillation unit, thermometer and receiver. 13.0 g of isopropanol are removed by distillation, and remaining alcohol is subsequently removed under reduced pressure.

Yield: 35.6 g (cal. 34.6 g) of a resinous substance of formula

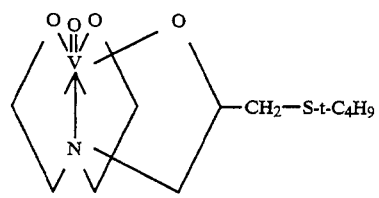

Example 8

With stirring, a mixture of 25.1 g of the compound t—$C_4H_9$—S—$CH_2$—CH(OH)—$CH_2$—N(—$CH_2$—CH$_2$—OH)$_2$, 20.2 g of vanadyl ethylate and 150 ml of toluene are heated for 30 minutes under reflux. After cooling to 20° C., the precipitated crystals are isolated by filtration, washed with petroleum ether and dried, giving 27.7 g (88% of theory) of the compound of formula in the form of pale yellow crystals which melt at 148°–151° C.

The compounds of Examples 9, 10, 11 and 12 (Table II) are prepared in similar manner to Example 8. Where non-crystalline final products are obtained, the solvent toluene/alcohol is removed by distillation upon completion of the reaction.

TABLE II

| Ex. | Formula | Analyt. data | Comments |
|---|---|---|---|
| 9 | | wax (olive green) $n_D^{20}$: 1.4769 of sol. (1:1) in DMF | recrystallised from toluene/petroleum ether |
| 10 | | resin (colourless) m.p.: 85–90° C. | Sb triisopropylate was used as metal compd. |
| 11 | | resin (colourless) $n_D^{20}$: 1.5258 of sol. (1:1) in toluene | Ti(—O-n-$C_4H_9$)$_4$ was used as metal compd. |

TABLE II-continued

| Ex. | Formula | Analyt. data | Comments |
| --- | --- | --- | --- |
| 12 | 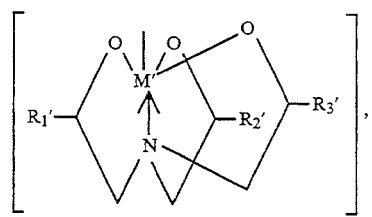 | viscous liquid $n_D^{20}$: 1.4813 | aluminium triisopropylate was used as metal compound |

Example 13

Test for suitability as extreme pressure and antiwear additive ASTM Standard method D-2783-81 using the Shell four-ball apparatus is used for the test of suitability as antiwear additive. The base oil used is STOCK 305 (ex Mobil), to which the amount of compound indicated in the Table is added in accordance with the respective Example. The average wear scar diameter is measured at a load of 400N after a 2 hour operation at 60° C. (in mm).

The results are reported in Table III. Small diameter of the wear scar denotes suitability as antiwear additive.

TABLE III

| Compound of Example | Amount of additive [%] | WSD [mm] |
| --- | --- | --- |
| without additive | | 0.96 |
| 5 | 0.5 | 0.86 |
| | 1.0 | 0.86 |

What is claimed is:

1. A composition comprising
a) an internal combustion engine fuel, and
b) at least one compound of the formula I

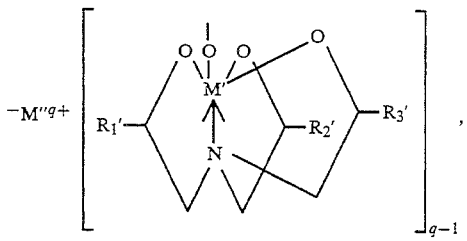 (I)

wherein $R_1$ is $-(CH_2-X)_n-R$, where $X=-S-$ or $-O-$, $n=0$ or 1 and R is an alkyl group of 1 to 18 carbon atoms, a phenyl group, a phenyl group which is substituted by at least one $C_1-C_{18}$alkyl group, a phenyl-($C_1-C_4$alkylene) group or a phenyl-($C_1-C_4$alkylene) group which is substituted by at least one $C_1-C_4$alkyl group, or $R_1$ is an alkyl group of 1 to 18 carbon atoms which is substituted by at least one OH group, or $R_1$ is a

group in which the alkyl moiety contains 1 to 18 carbon atoms, and $R_2$ and $R_3$ are the same or different and are $-H$ or, independently of $R_1$, have the same meanings as $R_1$, and M is B, Al, Fe, Cr, Sb or Bi, or M is a group $M'-R'$ or a group $M'-OR''$, where $M'$ is Ti, Zr or Sn, and $R'$ and $R''$ are $C_1-C_{18}$alkyl or $R'$ is

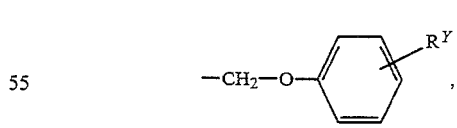

wherein $M'$ is as defined above, and $R_1'$, $R_2'$ and $R_3'$ have the meanings of $R_1$, $R_2$ and $R_3$, or $R''$ is Li, Na or K or is

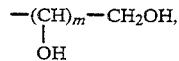

wherein $M'$ is as defined above and $M''$ is Mg, Ca, B, Al, Fe, Cr, Sb, Bi, Zn, Ti, Ni or Cu, q has the valency of $M''$, and $R_1'$, $R_2'$ and $R_3'$ have the respective meanings of $R_1$, $R_2$ and R, or M is VO.

2. A composition according to claim 1 comprising a compound of formula I, wherein M is B, Al, Fe, VO or Ti—O—$C_4$-$C_8$alkyl.

3. A composition according to claim 1 comprising a compound of formula I, wherein $R_1$ is —$CH_2$—S—C-4-$C_{12}$alkyl, —$CH_2$—O—$C_4$-$C_{12}$alkyl, —$CH_2$—O—CO—$C_4$-$C_{12}$alkyl, —$CH_2$—O—⟨phenyl⟩—$R^Y$, where $R^Y$=alkyl of 4 to 18 carbon atoms, or is —(CH)$_m$—$CH_2OH$,
        |
        OH wherein m=1, 2 or 3, and $R_2$ and $R_3$ are each independently of the other —H or $R_1$.

4. A composition according to claim 1 comprising a compound of formula I, wherein R1 is as defined in claim 1 and $R_2$ and $R_3$ are hydrogen, or wherein $R_1$ and $R_2$, with the exception of hydrogen, are as defined in claim 1 and $R_3$ is hydrogen.

5. A composition according to claim 1 comprising a compound of formula I, wherein $R_1$ is —$CH_2$—S—$C_4$-$C_{12}$alkyl, —$CH_2$—O—CO—$C_8$—$C_{12}$alkyl and $R_2$ and $R_3$ are —H.

6. A composition according to claim 1 comprising a compound of formula I, wherein $R_1$ and $R_2$ are —$CH_2$—S—$C_4$-$C_{12}$alkyl and $R_3$ is —H.

7. A composition according to claim 1 comprising at least one of the compounds of formula I

and

8. A composition according to claim 1, comprising
a) a diesel engine fuel, and
b) at least one compound of the formula I.

* * * * *